(12) United States Patent
Zhou et al.

(10) Patent No.: US 12,023,546 B2
(45) Date of Patent: Jul. 2, 2024

(54) DENTAL APPLIANCE

(71) Applicant: Wuxi EA Medical Instruments Technologies Limited, Wuxi (CN)

(72) Inventors: Ketuo Zhou, Shanghai (CN); Meng Wang, Shanghai (CN); Lei Huang, Shanghai (CN)

(73) Assignee: Wuxi EA Medical Instruments Technologies Limited, Wuxi (CN)

( * ) Notice: Subject to any disclaimer, the term of this patent is extended or adjusted under 35 U.S.C. 154(b) by 965 days.

(21) Appl. No.: 16/975,557

(22) PCT Filed: May 8, 2019

(86) PCT No.: PCT/CN2019/085968
§ 371 (c)(1),
(2) Date: Aug. 25, 2020

(87) PCT Pub. No.: WO2020/038021
PCT Pub. Date: Feb. 27, 2020

(65) Prior Publication Data
US 2020/0398107 A1    Dec. 24, 2020

(30) Foreign Application Priority Data

Aug. 23, 2018 (CN) .......................... 201810972121.0

(51) Int. Cl.
*A63B 23/03* (2006.01)
*A61C 7/08* (2006.01)
(Continued)

(52) U.S. Cl.
CPC .............. *A63B 23/032* (2013.01); *A61C 7/08* (2013.01); *A61C 19/06* (2013.01);
(Continued)

(58) Field of Classification Search
CPC ... A63B 23/032; A63B 2071/086; A61C 7/08; A61C 19/06; A61F 5/05891; B33Y 50/00
See application file for complete search history.

(56) References Cited

U.S. PATENT DOCUMENTS 3,286,576 A * 11/1966 West ..................... A63B 23/032
                                                                                128/859
4,637,796 A *  1/1987 Korn ........................ A61C 7/00
                                                                                    433/7
(Continued)

FOREIGN PATENT DOCUMENTS

CN          2384594 Y      6/2000
CN        201469249 U      5/2010
(Continued)

OTHER PUBLICATIONS

Feng, Hailan, "Guidance for Stomatology", Peking University Medical Press (2013).

(Continued)

*Primary Examiner* — Tarla R Patel
(74) *Attorney, Agent, or Firm* — FORGE IP, PLLC

(57) ABSTRACT

In one aspect of the present application, a dental appliance for isolating jaws from facial muscles is provided, the dental appliance is substantially in the shape of an elongated plate curved according to dental arches, and is received between the jaws and the facial muscles when it is worn, the dental appliance comprises: buccal shields located at both ends of the dental appliance and configured to isolate posterior teeth from facial muscles; and labial bumpers located in the middle of the dental appliance and configured to isolate anterior teeth from facial muscles, wherein the buccal shields and the labial bumpers form an integral piece.

8 Claims, 4 Drawing Sheets

(51) Int. Cl.
  *A61C 19/06* (2006.01)
  *A61F 5/058* (2006.01)
  *A63B 71/08* (2006.01)
  *B33Y 50/00* (2015.01)

(52) U.S. Cl.
  CPC .......... *A61F 5/05891* (2013.01); *B33Y 50/00* (2014.12); *A63B 2071/086* (2013.01)

(56) References Cited

U.S. PATENT DOCUMENTS

| | | | | | |
|---|---|---|---|---|---|
| 4,797,093 | A | * | 1/1989 | Bergersen | ................ A61C 7/00 433/7 |
| 4,881,896 | A | * | 11/1989 | Bergersen | ................ A61C 7/06 433/7 |
| 5,037,295 | A | * | 8/1991 | Bergersen | ................ A61C 7/08 433/7 |
| 7,458,810 | B2 | * | 12/2008 | Bergersen | .............. B33Y 80/00 433/6 |
| 9,585,732 | B2 | * | 3/2017 | Piancino | ................ A61F 5/566 |

FOREIGN PATENT DOCUMENTS

| | | | | | |
|---|---|---|---|---|---|
| CN | 101801305 | | 8/2010 | | |
| CN | 101801305 A | * | 8/2010 | ............... | A61C 7/08 |
| CN | 201668522 | | 12/2010 | | |
| CN | 105662679 | | 6/2016 | | |
| CN | 105662679 A | * | 6/2016 | ............... | A61F 5/01 |
| CN | 205459251 | | 8/2016 | | |
| CN | 206623475 U | | 11/2017 | | |
| CN | 105142740 B | | 12/2017 | | |
| CN | 207152659 | | 3/2018 | | |
| CN | 107865705 | | 4/2018 | | |
| CN | 107865705 A | * | 4/2018 | ............... | A61C 7/08 |
| CN | 108420553 | | 8/2018 | | |
| CN | 209122512 | | 7/2019 | | |
| CN | 209122512 U | * | 7/2019 | ........... | A63B 23/032 |
| CN | 209630534 U | * | 11/2019 | | |
| CN | 217828109 U | * | 11/2022 | | |
| CN | 218686059 U | * | 3/2023 | | |
| KR | 20100089823 A | * | 9/2008 | | |
| WO | WO-9308761 A1 | * | 5/1993 | ............... | A61C 7/08 |
| WO | WO-2009034205 A1 | * | 3/2009 | ............... | A61C 7/08 |

OTHER PUBLICATIONS

Fleming, Padhraig, "Orthodontic Functional Appliances: Theory and Practice", John Wiley and Sons, Ltd (2017).
Fu, Minkui, "Orthodontics" (5th edition), People's Medical Publishing House (2007).
Lin, Jiuxiang, "Modern Orthodontics—Unity of Science and Art", China Medical Science and Technology Press (1995).
Sun, Jianli, "A Meliorative FR-III Appliance in Treatment of Class III Malocclusion with Mixed Dentition"; Dissertation for the Degree of Master, Zhengzhou University (2010).
Tenti, Federico V., "Atlas of Orthodontic Applicances"; Italy (1986).
Zhao, Shijie, "Oral and Maxillofacial Anatomy", Peking University Medical Press (2005).

* cited by examiner

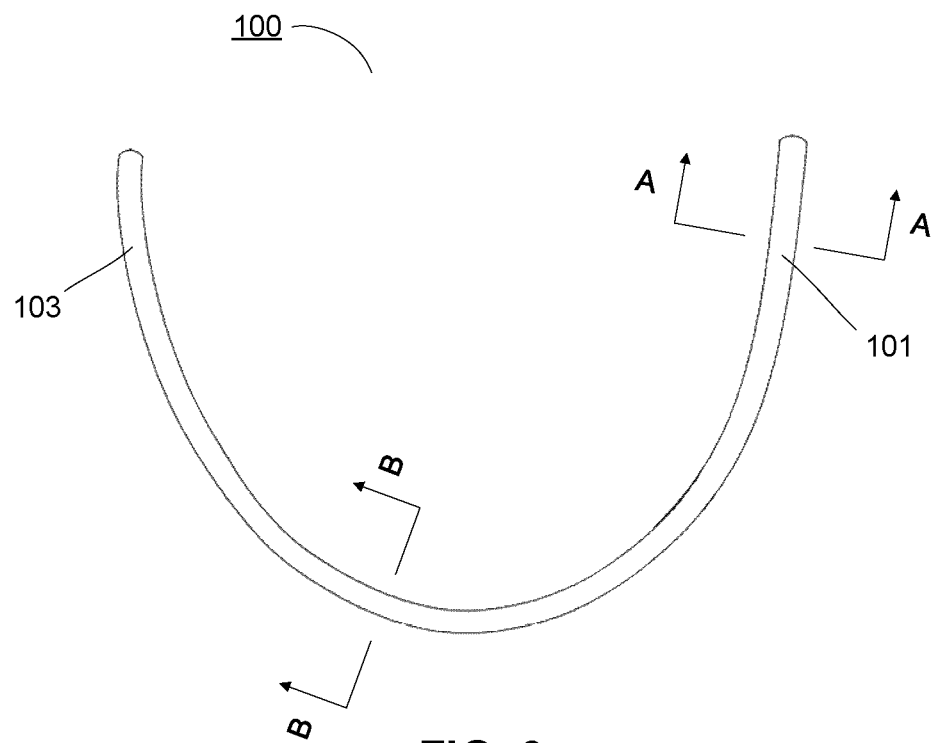
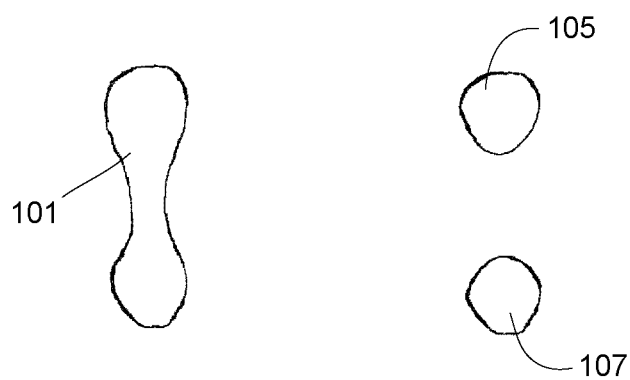 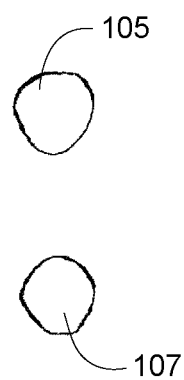
FIG. 3
FIG. 4A        FIG. 4B

DENTAL APPLIANCE

FIELD OF THE APPLICATION

The present application generally relates to a dental appliance for isolating facial muscles from jaws.

BACKGROUND

Orofacial myofunctional therapy (abbreviated as "OMT") is to perform facial neuromuscular re-education on a patient having orofacial myofunctional disorders, to establish a new and proper balance of facial muscles acting on the dental arches, and therefore to promote alveolar bone remodeling and normal growth and development of dentofacial structure. Basically, OMT is a therapy that focuses on causes of diseases.

Currently, a commonly used appliance in OMT is Frankel appliance, which usually includes resin buccal shields and labial bumpers connected using steel wires, and is fixed in oral cavity. To fabricate a Frankel appliance, a doctor needs to design and make buccal shields, labial bumpers and steel wires for connecting and fixing the buccal shields and labial bumpers based on a plaster model of teeth according to experiences. The whole process is laborious and time consuming and the cost is very high.

In view of the above, it is necessary to provide a new dental appliance to isolate facial muscles from jaws, which can be used to train facial muscles and/or perform orofacial myofunctional therapy.

SUMMARY

In one aspect, the present application provides a dental appliance for isolating jaws from facial muscles, the dental appliance is substantially in the shape of an elongated plate curved according to dental arches, and is received between the jaws and the facial muscles when it is worn, the dental appliance includes: buccal shields located at both ends of the dental appliance and configured to isolate posterior teeth from facial muscles; and labial bumpers located in the middle of the dental appliance and configured to isolate anterior teeth from facial muscles, wherein the buccal shields and the labial bumpers form an integral piece.

In some embodiments, when the dental appliance is worn, its upper and lower sides may be substantially located at bottoms of a maxillary vestibular groove and a mandibular vestibular groove, respectively.

In some embodiments, contours of the upper and lower sides of the dental appliance may match contours of the bottoms of the maxillary and mandibular vestibular grooves, respectively.

In some embodiments, contours of the upper and lower sides of the dental appliance have inwardly-recessed structures formed thereon to avoid lip ties when the dental appliance is worn.

In some embodiments, the dental appliance may further have an opening formed thereon such that crowns of teeth #1-4 of upper and lower jaws are exposed when the dental appliance is worn.

In some embodiments, a hollowed portion may be formed on the buccal shields on both ends of the dental appliance to reduce weight.

In some embodiments, a cross-sectional contour of the buccal shields may be wider on upper and lower sides and narrower in the middle.

In some embodiments, a cross-sectional contour of the labial bumpers may be one of the following: wider on upper and lower sides and narrower in the middle; wider on the upper side and narrower on the lower side; and narrower on the upper side and wider on the lower side.

In some embodiments, when the dental appliance is worn, a gap may be formed between the dental appliance and at least one of maxillary gingiva and mandibular gingiva.

In some embodiments, a layer of thin film made of a soft material may be formed on the surface of the dental appliance to improve the wearing comfort.

In another aspect, the present application provides a method of fabricating a dental appliance for isolating jaws from facial muscles, comprising: obtaining a patient's oral cavity data comprising the length and curve geometry of dental arches and distance between bottoms of maxillary and mandibular vestibular grooves; generating a 3D digital model representing the dental appliance based on the oral cavity data, where the 3D digital model is substantially in a shape of a curved elongated plate whose curve geometry substantially matches that of the dental arches, a buccal shield is formed at both ends of the 3D digital model to isolate posterior teeth from facial muscles, and labial bumpers are formed in a middle section of the 3D digital model to isolate anterior teeth from facial muscles; and using the 3D digital model to control a device to fabricate the dental appliance.

In some embodiments, the oral cavity data may further comprise contours of the bottoms of the maxillary and mandibular vestibular grooves so that contours of upper and lower sides of the 3D digital model substantially match the contours of the bottoms of the maxillary and mandibular vestibular grooves, respectively.

In some embodiments, the buccal shields and the labial bumpers in the 3D digital model may form an integral piece.

In some embodiments, the device may be 3D printing device.

In some embodiments, the method of fabricating the dental appliance may further comprise: obtaining dimensions of the buccal shields and labial bumpers, wherein the 3D digital model may be generated based on the oral cavity data and the dimensions of the buccal shields and labial bumpers.

In some embodiments, an opening is formed at a middle section of the 3D digital model so that crowns of teeth #1-4 of the upper and lower jaws are exposed when the appliance is worn.

In some embodiments, a hollowed portion is formed on each of the buccal shields of the 3D digital model to reduce the weight of the dental appliance.

BRIEF DESCRIPTION OF THE DRAWINGS

The above and other features of the present application will be further illustrated below with reference to figures and their detailed description. It should be appreciated that these figures only show several exemplary embodiments according to the present application, so they should not be construed as limiting the protection scope of the present application. Unless otherwise specified, the figures are not necessarily drawn to scale, and similar reference numbers therein denote similar components.

FIG. 3 is a top view of the dental appliance shown in FIG. 1;

FIG. 4A is a cross-sectional view at section A-A of the dental appliance shown in FIG. 3;

FIG. 4B is a cross-sectional view at section B-B of the dental appliance shown in FIG. 3;

DETAILED DESCRIPTION OF ILLUSTRATED EMBODIMENTS

In the following detailed description, reference is made to the accompanying drawings, which form a part thereof. Exemplary embodiments in the detailed description and figures are only intended for illustration purpose and not meant to be limiting. Inspired by the present application, those skilled in the art can understand that other embodiments may be utilized and other changes may be made, without departing from the spirit or scope of the present application. It will be readily understood that aspects of the present application described and illustrated herein can be arranged, replaced, combined, separated and designed in a wide variety of different configurations, all of which are explicitly contemplated and make part of the present application.

After a lot of work, the Inventors of the present application developed a novel dental appliance which selectively isolates facial muscles from jaws, and is used to train facial muscles and/or perform orofacial myofunctional therapy, to establish a new proper balance of facial muscles, and thereby promote alveolar bone remodeling and normal growth and development of dentofacial structure. Meanwhile, the Inventors of the present application further developed a method of fabricating the dental appliance.

Figure 1:
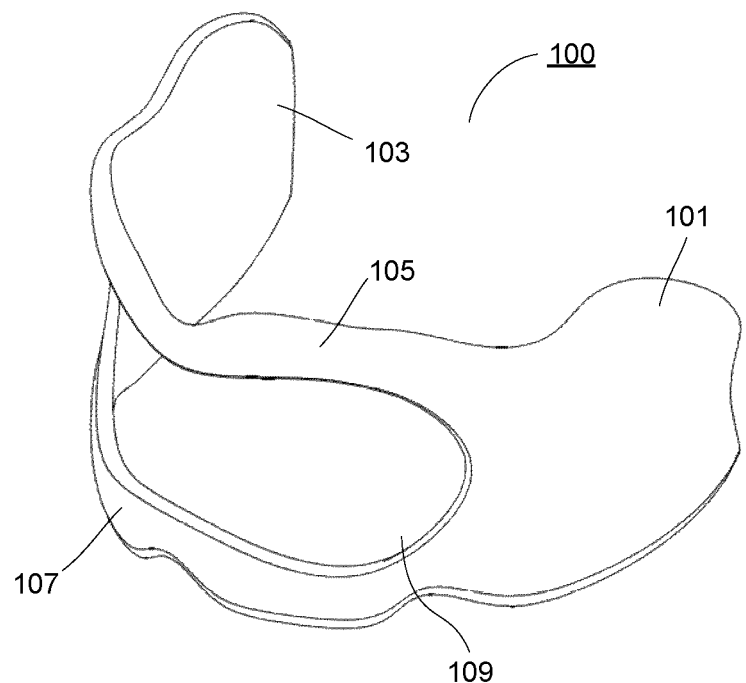
FIG. 1 schematically illustrates a dental appliance in one embodiment of the present application.
Figure 2:
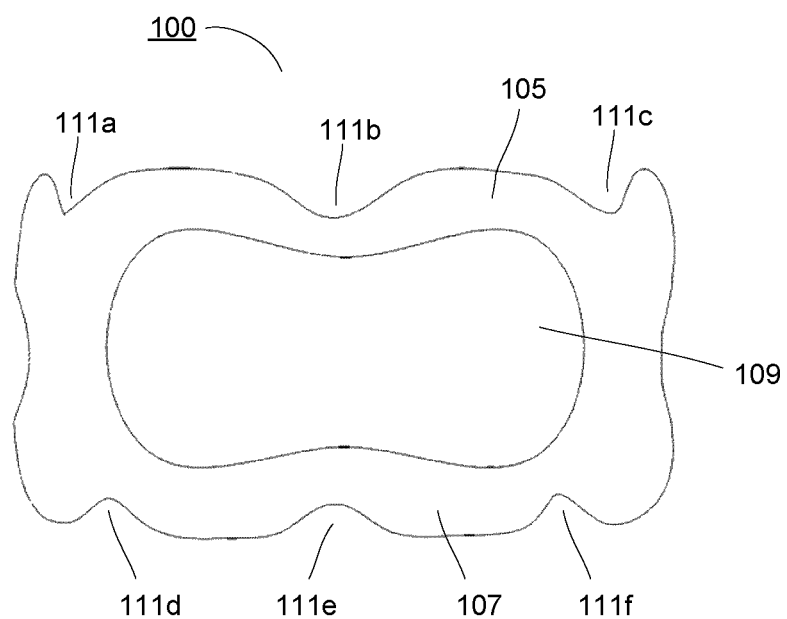
FIG. 2 is a front view of the dental appliance shown in FIG. 1.

Referring to FIG. 1 to FIG. 3, a dental appliance 100 in one embodiment of the present application is illustrated. FIG. 1 is a perspective view of the dental appliance 100, FIG. 2 is a front view of the dental appliance 100, and FIG. 3 is a top view of the dental appliance 100.

The dental appliance 100 is generally a thin plate curved into C shape, it includes buccal shields 101 and 103, a maxillary labial bumper 105, a mandibular labial bumper 107, an opening 109 and grooves 111a-111f. The dental appliance 100 is to be worn between the facial muscles and jaws and is generally located on the labial sides of the jaws.

The buccal shields 101 and 103 are respectively located adjacent to two ends of the C shape of the dental appliance 100 and are used to isolate the jaws from muscles in the cheek region. In one embodiment, the buccal shield 101 may extend from a maxillary vestibular groove to a mandibular vestibular groove, its distal end covers the last tooth, and its mesial end reaches distal ends of corresponding canines.

Referring to FIG. 4A, it is a cross-sectional view at section A-A of the buccal shield 101 shown in FIG. 3. In one embodiment, the cross-section of the upper and lower sides of the buccal shield 101 may be teardrop-shaped to avoid stimulating lip ties and corresponding muscles. The buccal shield 103 may have cross sections similar to that of the buccal shield 101.

The maxillary labial bumper 105 is located at the vestibular groove above the maxillary incisors and is used to isolate the upper jaw from the muscles in the lip region.

The mandibular labial bumper 107 is located at the vestibular groove below the mandibular incisors and is used to isolate the lower jaw from the muscles in the lip region.

Referring to FIG. 4B, it is a cross-sectional view at section B-B of the maxillary labial bumper 105 and the mandibular labial bumper 107 shown in FIG. 3. In one embodiment, the cross-section of the maxillary labial bumper 105 and the mandibular labial bumper 107 may be teardrop-shaped to avoid stimulating lip ties and corresponding muscles.

The grooves 111a-111f are formed at the upper and lower edges of the dental appliance 100 to avoid lip ties to improve the wearing comfort. In one embodiment, the grooves 111a-111f may be rounded and smooth dovetail grooves. Inspired by the present application, it is understood that the grooves 111a-111f may be in any other suitable shapes such as an arcuate shape.

An opening 109 is formed and surrounded by the buccal shields 101 and 103, the maxillary labial bumper 105 and the mandibular labial bumper 107. The teeth within the range of the opening 109 may be exposed to prevent the dental appliance 100 from colliding with these teeth and thereby affecting the forces received by these teeth, particularly teeth that are proclined.

In one embodiment, the opening 109 may cover crowns of all teeth from canines to incisors of both upper and lower jaws.

In one embodiment, the buccal shields 101 and 103, the maxillary labial bumper 105 and the mandibular labial bumper 107 may form an integral piece, i.e., their surfaces may be continuous.

Figure 5:
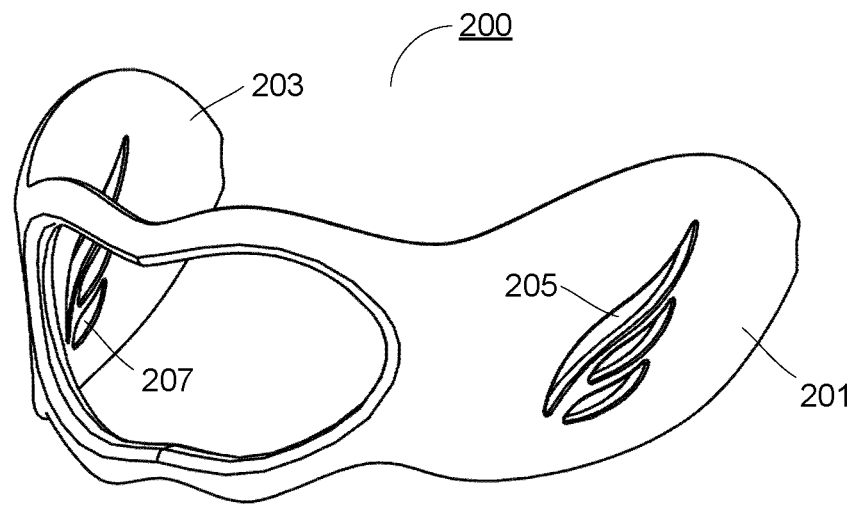
FIG. 5 schematically illustrates a dental appliance in another embodiment of the present application.

Referring to FIG. 5, it schematically illustrates a dental appliance 200 in another embodiment of the present application.

To reduce the weight of the dental appliance 200 and improve the wearing comfort, hollow portions 205 and 207 may be formed on the buccal shields 201 and 203 on both ends, respectively. The hollowed portions 205 and 207 may be in any suitable shape.

Figure 6:
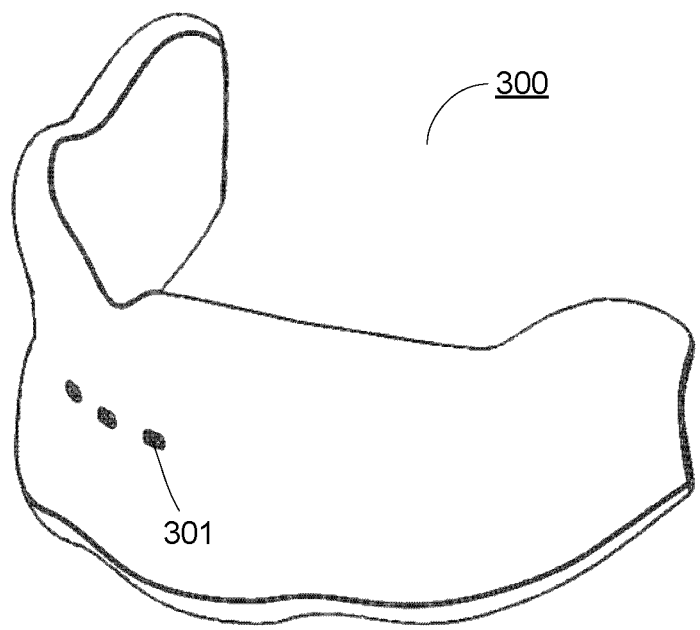
FIG. 6 schematically illustrates a dental appliance in a further embodiment of the present application.

Referring to FIG. 6, it schematically illustrates a dental appliance 300 in a further embodiment of the present application.

The dental appliance 300 is substantially a C-shaped plate having a certain width, and no opening is formed in its middle section, instead, multiple breathing holes 301 are formed to help patients to transit from oral breathing to nasal breathing. Since the breathing holes 301 are small, they are able to limit the habit of oral breathing but do not cut off the oral breathing suddenly.

In one embodiment, the size of the breathing holes 301 may be about 1-2 mm, and their shapes may be circle, rectangle, ellipse or any other suitable shapes. The number of the breathing holes 301 may be one, two, three, four, etc., and the breathing holes 301 may be arranged in one row or two rows.

In one embodiment, maxillary labial bumper and mandibular labial bumper may be formed according to specific situations and needs of cases. For example, the dental appliance may be provided with only the maxillary labial bumper, only the mandibular labial bumper, or both the maxillary and mandibular labial bumpers.

In one embodiment, a soft material may be used to form the surface of the dental appliance to improve the wearing comfort, e.g., a gelatin.

In one embodiment, a support may be provided inside the dental appliance to improve its mechanical strength, which extends from the buccal shield at one end, through one or both of the labial bumpers, to the buccal shield at the other end. The support may be made of a material with high rigidity, e.g., a metal. In one embodiment, the support may be a steel wire bent into C shape.

In one embodiment, the geometry of the dental appliance and how it contact various parts in the oral cavity may be determined according to specific situations and needs of cases. For example, for Angle Class III malocclusion, the maxillary buccal shield and maxillary labial bumper may be used to isolate the facial muscles from the jaws, release the limiting force of the facial muscles, and meanwhile stimulate growth of periosteum to cause the upper jaw to continue to grow; the mandibular buccal shield and mandibular labial bumper may be used to transmit forces generated by facial muscles, and limit the growth of the lower jaw.

Figure 7:
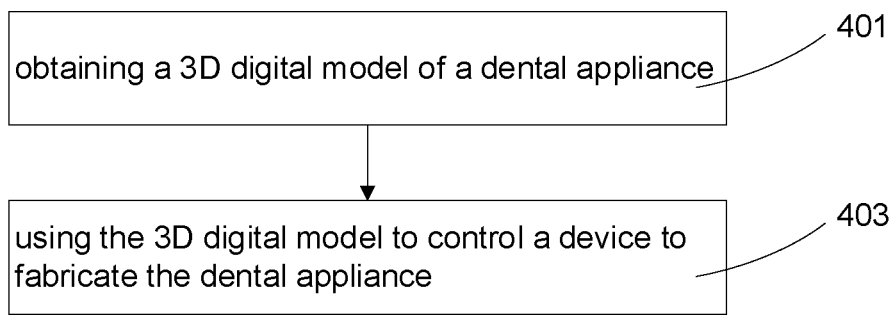
FIG. 7 illustrates a schematic flow chart of a method of fabricating the dental appliance in an embodiment of the present application.

Referring to FIG. 7, it schematically illustrates a flow chart of a method 400 of fabricating the dental appliance in one embodiment of the present application.

In 401, a 3D digital model representing the dental appliance is obtained.

In one embodiment, the dental appliance may be highly customized, i.e., the dental appliance may be designed and fabricated based on a patient's oral cavity. An example of obtaining the 3D digital model representing the dental appliance based on customization will be described in detail below.

In one embodiment, data of the patient's oral cavity may be obtained by directly measuring the patient's oral cavity. In another embodiment, dental impression may be taken using silicone material, and then the data of the patient's oral cavity may be obtained by measuring the model. In a further embodiment, the patient's oral cavity may be scanned to obtain a 3D digital model, and then the 3D digital model be measured to obtain the data of the patient's oral cavity. Examples of scanning device may comprise intra-oral scanner, Cone Beam Computed Tomography (CBCT), spiral Computed Tomography, etc.

Figure 8:
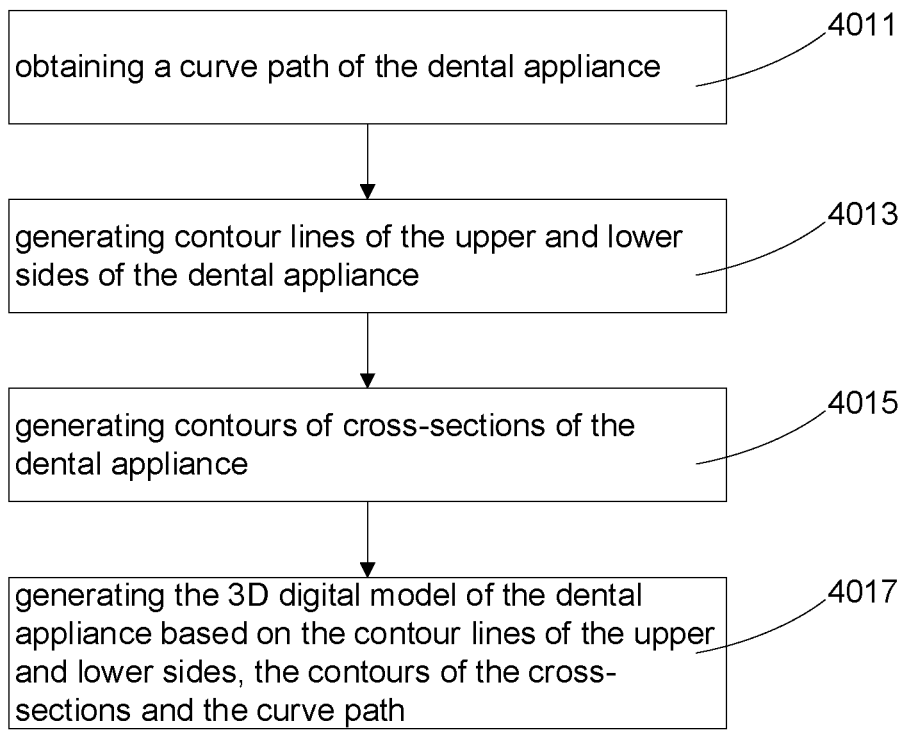
FIG. 8 illustrates a schematic flow chart of generating a 3D digital model representing the dental application in one embodiment of the present application.

Referring to FIG. 8, it schematically illustrates a flow chart of obtaining a 3D digital model representing the dental application in one embodiment.

In 4011, a curve path of the dental appliance is obtained.

In one embodiment, two dental arches may be taken as the curve path of the dental appliance.

In one embodiment, the gingival zenith of tooth #1 may be moved towards the root by a predetermined distance, and an upper reference plane and a lower reference plane parallel to the occlusal surface may be created based on the moved gingival zenith. In one embodiment, the predetermined distance may be determined according to the patient's specific situations and the functions of the dental appliance, e.g., it may be 4 mm.

Then, the outer surfaces of soft tissues of alveolar bones may be pushed outward by predetermined distances, and 7 key points may be selected on each of the intersecting lines of the pushed outer surfaces and the reference planes. A dental arch may be generated by interpolation based on a group of the 7 key points.

In one embodiment, the predetermined distances, by which the outer surfaces of the soft tissues of alveolar bones shall be pushed outward, may be determined based on the patient's specific situations and functions of the dental appliance. For example, the dental arch key point at the distal end of the tooth #7 may be 2.5 mm away from the outer surface of the soft tissue of the alveolar bone; the dental arch key point in the middle of the tooth #6 may be 2.8 mm away from the outer surface of the soft tissue of the alveolar bone; the dental arch key point at the mesial end of the tooth #3 may be 3.5 mm away from the outer surface of the soft tissue of the alveolar bone; the dental arch key point in the middle of the tooth #1 may be 3.5 mm away from the outer surface of the soft tissue of the alveolar bone.

In 4013, contours of upper and lower sides of the dental appliance are generated.

In one embodiment, contours of the bottoms of the maxillary and mandibular vestibular grooves may be taken as contours of the upper and lower sides of the dental appliance, respectively. In one embodiment, nine key points may be selected on a contour of the bottom of a vestibular groove, and contour of the bottom of the vestibular groove may be obtained by interpolation based on the nine key points.

Before the contours of the bottoms of the maxillary and mandibular vestibular grooves are obtained, the upper and lower dental arch may be straightened, i.e., the arc lengths of the two dental arches may be calculated, and two straight line segments whose lengths are equal to the two dental arches respectively may be generated, wherein the two straight line segments respectively lie on the planes on which the key points of the two dental arches lie. A plane passing the two straight lines and being perpendicular to the occlusal plane is defined as a mapping plane.

In one embodiment, the contour line of the bottom of the maxillary vestibular groove lies on a curved surface, which the upper dental arch lies on and is perpendicular to the occlusal plane.

In one embodiment, nine key points of the contour line of the bottom of the maxillary vestibular groove may be selected according to the following method: the distal end of gingival margin of tooth #7 is taken as a key point; the midpoint of the gingival margin of tooth #6 is moved towards the bottom of the groove by a certain distance (e.g., the length of the crown of the tooth), and is taken as a key point; the midpoint of the gingival margin of tooth #4 is moved towards the bottom of the groove by a certain distance (e.g., half the length of the crown of the tooth), and is taken as a key point; the distal end of the gingival margin of tooth #2 is moved towards the bottom of the groove by a certain distance (e.g., the length of the crown of the tooth), and is taken as a key point; the midpoint of the gingival margin of tooth #1 is moved towards the bottom of the groove by a certain distance (e.g., half the length of the crown of the tooth), and is taken as a key point.

In one embodiment, the contour line of the bottom of the mandibular vestibular groove lies on a curved surface, which the lower dental arch baseline lies on and is perpendicular to the occlusal plane.

In one embodiment, nine key points of the contour line of the bottom of the mandibular vestibular groove may be selected according to the following method: the distal end of gingival margin of tooth #7 is taken as a key point; the midpoint of the gingival margin of tooth #5 is moved towards the bottom of the groove by a certain distance (e.g., the length of the crown of the tooth), and is taken as a key point; the midpoint of the gingival margin of tooth #3 is moved towards the bottom of the groove by a certain distance (e.g., half the length of the crown of the tooth), and is taken as a key point; the distal end of the gingival margin of tooth #2 is moved towards the bottom of the groove by a certain distance (e.g., the length of the crown of the tooth), and is taken as a key point; the midpoint of the gingival margin of tooth #1 is moved towards the bottom of the groove by a certain distance (e.g., half the length of the crown of the tooth), and is taken as a key point.

In one embodiment, lines that connect the key points of teeth #7 facing each other of the upper and lower jaws may be perpendicular to the occlusal plane; lines that connect the key points of teeth #1 facing each other of the upper and lower jaws may be perpendicular to the occlusal plane; there is an interpolation point on the contour line of the bottom of the mandibular vestibular groove, and a line that connect the interpolation point and the key point of the tooth #4 is perpendicular to the occlusal plane; there is an interpolation point on the upper jaw, and a line that connect the interpolation point and the key point of tooth #3 of the lower jaw is perpendicular to the occlusal plane.

Then, the contour lines of the bottoms of the maxillary and mandibular vestibular grooves are straightened and mapped to the mapping plane.

In one embodiment, the contour lines of the bottoms of the maxillary and mandibular vestibular grooves may be obtained based on analysis of big data.

In 4015, contours of cross-sections of the dental appliance are generated.

In one embodiment, contours of seven cross-sections may be generated (four types in total), and these cross-sections are left-right symmetrical. The 3D model of the dental appliance may be obtained by scanning based on these seven cross-sectional contours.

In one embodiment, eight key points may be selected with respect to a contour line of one cross-section, and then interpolation is performed based on these eight key points to obtain the contour line.

In on embodiment, the cross-section is shaped to be substantially wider at upper and lower ends, and narrower in the middle.

In one embodiment, contours of the cross-sections may be generated according to the following methods:

The first type of contours of cross-sections: the upper and lower vertices are respectively two key points of the upper and lower teeth #7 on the contour lines of the bottoms of the maxillary and mandibular vestibular grooves. There is one key point on each of opposite sides of the upper and lower widest parts of the contour, the width is about 1.8 mm, and each of these key points is about 0.9 mm away from adjacent upper and lower key points on the same side; there is one key point on each of opposite sides of the middle narrowest part, and the width is about 1.5 mm.

The second type of contours of cross-sections: the upper and lower vertices are respectively the key point of tooth #4 of the upper jaw on the contour line of the bottom of the maxillary vestibular groove and an interpolation point on the contour line of the bottom of the mandibular vestibular groove, which interpolation point corresponds to the key point of tooth #4. There is one key point on each of opposite sides of the upper and lower widest parts, the width is about 2.4 mm, and each of these key points is about 1.2 mm away from adjacent upper and lower key points on the same side; there is one key point on each of opposite sides of the middle narrowest part, and the width is about 2 mm.

The third type of contours of cross-sections: the lower vertex is the key point of tooth #3 on the contour line of the bottom of the mandibular vestibular groove, and the upper vertex is an interpolation point on the contour line of the bottom of the maxillary vestibular groove, which interpolation point corresponds to the key point of tooth #3. There is one key point on each of opposite sides of the upper and lower widest parts, the width is about 3 mm, and each of these key points is about 1.5 mm away from adjacent upper and lower key points on the same side; there is one key point on each of opposite sides of the middle narrowest part, and the width is about 2.6 mm.

In one embodiment, three types of labial bumper configurations may be provided according to functions needed: standard labial bumper configuration, upper labial bumper configuration and lower labial bumper configuration.

In one embodiment, for the standard labial bumper configuration, the thickness of the upper and lower labial bumpers may be set to about 4 mm. For the upper labial bumper configuration, the thickness of the upper labial bumper may be set to about 3.5 mm, and the thickness of the lower labial bumper may be set to about 1.8 mm. For the lower labial bumper configuration, the thickness of the lower labial bumper may be set to about 3.5 mm, and the thickness of the upper labial bumper may be set to about 1.8 mm.

In one embodiment, if the upper labial bumper configuration is selected, on a third type of cross-sectional contour, there is one key point on each opposite sides of the widest part corresponding to the upper jaw, the width is about 3.5 mm; there is one key point on each of opposite sides of the middle part, and the width is about 2 mm; there is one key point on each of opposite sides of the widest part corresponding to the lower jaw, the width is about 1.8 mm, and each of them is about 0.9 mm away from the lowest key point.

In one embodiment, if the lower labial bumper configuration is selected, on a third type cross-sectional contour, there is one key point on each opposite sides of the widest part corresponding to the lower jaw, the width is about 3.5 mm; there is one key point on each opposite sides of the middle part, and the width is about 2 mm; there is one key point on each opposite sides of the widest part corresponding to the upper jaw, the width is about 1.8 mm, and each of them is about 0.9 mm away from the uppermost key point.

The fourth type of cross-sectional contours: the upper and lower vertices are respectively two key points of the teeth #1 on the contour lines of the bottoms of the maxillary and mandibular vestibular grooves. There is one key point on each of opposite sides of the upper and lower widest parts, the width is about 3.5 mm, and each of these key points has adjacent upper and lower key points at the same side and is about 1.8 mm away from the adjacent upper and lower key points; there is one key point on each of opposite sides of the middle narrowest part, and the width is about 3 mm.

In one embodiment, if the upper labial bumper configuration is selected, on a fourth type of cross-sectional contour, there is one key point on each of opposite sides of the widest part corresponding to the upper jaw, the width is about 3.5 mm; there is one key point on each of opposite sides of the middle part, and the width is about 2 mm; there is one key point on each opposite sides of the widest part corresponding to the lower jaw, the width is about 1.8 mm, and they are about 0.9 mm away from the lowest key point.

In one embodiment, if the lower labial bumper configuration is selected, on a fourth type of cross-sectional contour, there is one key point on each of opposite sides of the widest part corresponding to the lower jaw, the width is about 3.5 mm; there is one key point on each of opposite sides of the middle part, and the width is about 2 mm; there is one key point on each opposite sides of the widest part corresponding to the upper jaw, the width is about 1.8 mm, and they are about 0.9 mm away from the uppermost key point.

In 4017, the 3D digital model is generated based on the upper and lower contour lines, cross-sectional contours and the curve path of the dental appliance.

A 3D digital model representing the dental appliance, which is flatted, may be obtained by scanning based on the contour lines of the upper and lower sides and the contours of the cross-sections of the dental appliance.

In one embodiment, structures such as an opening for anterior teeth, breathing holes and hollowed portions may be formed on the 3D digital model of the flatted main body of the dental appliance according to specific needs.

Then, the 3D digital model representing the flatted dental appliance is curved according to the dental arch to obtain the 3D digital model representing the C-shaped dental appliance.

It is understood that the above is only one example of obtaining the 3D digital model representing the dental appliance, wherein specific parameters may be adjusted according to specific situations and needs.

In one embodiment, some parameters of the dental appliance may be determined based on experiences, and may not be set strictly according to the above specific embodiment.

In 403, the 3D digital model representing the dental appliance is used to control a device to fabricate the dental appliance.

In one embodiment, the 3D digital model representing the dental appliance may be used to control a 3D printing device to fabricate the dental appliance. For example, a DDP4XL 3D printing device provided by envisionTEC GMBH may be used to fabricate the dental appliance. One of the following materials may be used: polymers of one or more of ethoxylated bisphenol A, methacrylic acid, amino-acrylic acid and other acrylic monomers with multi-functional groups.

In one embodiment, a material, whose elastic modulus is greater than 500 MPa and elastic range (including elastic ranges of bending and tension) is greater than 1%, is preferably selected to fabricate the dental appliance.

In another embodiment, the 3D digital model representing the dental appliance may be used to control a numerically-controlled machine tool to cut a blank to fabricate the dental appliance.

In a further embodiment, the 3D digital model representing the dental appliance may be used to control a device to fabricate a mould, and then the mould may be used to cast the dental appliance, for example, by injection molding.

In a further embodiment, the 3D digital model representing the dental appliance may be used to control a Stereo Lithography Apparatus to fabricate the dental appliance.

In one embodiment, before the dental appliance is actually fabricated, the dental appliance may be tested in simulation based on the 3D digital model representing the dental appliance, to determine whether it meets relevant mechanical performance requirements.

For example, the structure of the dental appliance according to the present application determines that its weak point lies in the mid-line of the incisors, so it is necessary to detect whether the dental appliance would break here during normal use. In one embodiment, two forces which are opposite in direction and equal in magnitude, both are towards lingual-side and static and loaded homogenously on surface, may be applied, and finite element analysis may be performed to analyze statics of the overall structure of the dental appliance.

It is found from research that forces received by the dental appliance according to the present application during use generally do not exceed 5N, and forces received by the dental appliance when it is worn or removed in a correct manner generally do not exceed 10N. In an embodiment, a factor of safety (e.g., 1.5) may be applied to test a boundary condition by applying a 15N force to the dental appliance under the above static conditions, and analyze its maximum local stress. If the maximum local stress does not exceed the yield strength of the material, it may be believed that the dental appliance is qualified.

While various aspects and embodiments have been disclosed herein, other aspects and embodiments will be apparent to those skilled in the art, inspired by the present application. The various aspects and embodiments disclosed herein are for illustration only and are not intended to be limiting, and the scope and spirit of the present application shall be defined by the following claims.

Likewise, the various diagrams may depict exemplary architectures or other configurations of the disclosed methods and systems, which are helpful for understanding the features and functions that can be included in the disclosed methods and systems. The claimed invention is not restricted to the illustrated exemplary architectures or configurations, and desired features can be achieved using a variety of alternative architectures and configurations. Additionally, with regard to flow diagrams, functional descriptions and method claims, the order in which the blocks are presented herein shall not mandate that various embodiments of the functions shall be implemented in the same order unless otherwise the context specifies.

Unless otherwise specifically specified, terms and phrases used herein are generally intended as "open" terms instead of limiting. In some embodiments, use of phrases such as "one or more", "at least" and "but not limited to" should not be construed to imply that the parts of the present application that do not use similar phrases intend to be limiting.

We claim:

1. A dental appliance for isolating jaws from facial muscles, the dental appliance being substantially in the a shape of an elongated plate curved according to dental arches and being received between the jaws and the facial muscles when it is worn, the dental appliance comprising:
   buccal shields located at both ends of the dental appliance and configured to isolate posterior teeth from facial muscles; and
   labial bumpers located in a middle of the dental appliance and configured to isolate anterior teeth from facial muscles, wherein the buccal shields and the labial bumpers form an integral piece;
   wherein the buccal shields and the labial bumpers define an opening configured to cover all canines and incisors, thereby preventing the dental appliance from colliding with the incisors and canines wherein contours of the upper and lower sides of the dental appliance have inwardly-recessed structures formed thereon to avoid lip ties when the dental appliance is worn.

2. The dental appliance of claim 1, wherein upper and lower sides of the dental appliance are substantially located at bottoms of a maxillary and a mandibular vestibular grooves, respectively, when the dental appliance is worn.

3. The dental appliance of claim 1, wherein contours of the upper and lower sides of the dental appliance match contours of bottoms of a maxillary and a mandibular vestibular grooves, respectively.

4. The dental appliance of claim 1, wherein a hollowed portion is formed on each of the buccal shields at both ends to reduce weight.

5. The dental appliance of claim 1, wherein contours of cross-sections of the buccal shields are wider on upper and lower sides and narrower in the middle.

6. The dental appliance of claim 1, wherein contours of cross-sections of the labial bumpers have a width in the middle different from a width at the upper side and the lower side.

7. The dental appliance of claim 1, wherein when the dental appliance is worn, a gap is formed between the dental appliance and at least one of maxillary gingiva and mandibular gingiva.

8. The dental appliance of claim 1, wherein a surface of the dental appliance is formed of a soft material for improving wearing comfort.

* * * * *